US008819990B2

(12) United States Patent
Zeelie et al.

(10) Patent No.: US 8,819,990 B2
(45) Date of Patent: Sep. 2, 2014

(54) PRESERVATION OF PLANT MATERIAL

(75) Inventors: Bernard Zeelie, Port Elizabeth (ZA); Ella-Christine Maske, Humansdorp (ZA); Shawn Gouws, Port Elizabeth (ZA)

(73) Assignee: African Floralush IP (Proprietary) Limited, Gauteng (ZA)

( * ) Notice: Subject to any disclaimer, the term of this patent is extended or adjusted under 35 U.S.C. 154(b) by 0 days.

(21) Appl. No.: 12/865,711

(22) PCT Filed: Feb. 5, 2009

(86) PCT No.: PCT/IB2009/050470
§ 371 (c)(1),
(2), (4) Date: Dec. 6, 2010

(87) PCT Pub. No.: WO2009/098653
PCT Pub. Date: Aug. 13, 2009

(65) Prior Publication Data
US 2011/0081507 A1     Apr. 7, 2011

(30) Foreign Application Priority Data
Feb. 5, 2008   (ZA) .................................. 2008/01238

(51) Int. Cl.
*A01N 3/00*     (2006.01)
*A01N 3/02*     (2006.01)

(52) U.S. Cl.
CPC ... *A01N 3/00* (2013.01); *A01N 3/02* (2013.01)
USPC .................. 47/58.1 CF; 47/58.1 R; 504/114; 504/115; 427/4; 428/17; 428/24

(58) Field of Classification Search
USPC .................. 428/17, 24; 427/4; 504/114, 115; 47/58.1 R, 58.1 C
See application file for complete search history.

(56) References Cited

U.S. PATENT DOCUMENTS

| 4,808,447 A | 2/1989 | Baker |
| 5,252,537 A * | 10/1993 | De Winter-Scailteur ..... 504/114 |
| 5,723,407 A * | 3/1998 | Midou et al. .................. 504/115 |
| 6,967,187 B1 * | 11/2005 | Hamley ......................... 504/114 |
| 2006/0172042 A1 * | 8/2006 | Clemons ........................ 426/103 |
| 2007/0111891 A1 | 5/2007 | Inao |
| 2007/0184080 A1 | 8/2007 | Keating |
| 2009/0227454 A1 * | 9/2009 | Jaiswal .......................... 504/114 |

FOREIGN PATENT DOCUMENTS

| EP | 0 091 092 | 10/1983 |
| EP | 1 016 343 | 7/2000 |
| JP | 53-104325 | 9/1978 |
| JP | 59-010304 | 1/1984 |
| JP | 04-021601 A | 1/1992 |
| JP | 07041401 A | 2/1995 |
| JP | 11341922 A | 12/1999 |
| JP | 2004-203815 A | 7/2004 |
| WO | WO-00/60937 | 10/2000 |
| WO | WO-02/065837 | 8/2002 |
| WO | WO-2005/004600 A1 | 1/2005 |
| WO | WO-2006/084104 A2 | 8/2006 |
| WO | WO-2006/084104 A3 | 8/2006 |
| WO | WO2007/127238 * | 8/2007 |

OTHER PUBLICATIONS

International Search Report for PCT/IB2009/050470, mailed on Jan. 25, 2010, 3 pages.

* cited by examiner

*Primary Examiner* — Lorna M Douyon
*Assistant Examiner* — Amina Khan
(74) *Attorney, Agent, or Firm* — Morrison & Foerster LLP

(57) ABSTRACT

This invention relates to a method for the preservation and/or dyeing of plant material including cut flowers. According to the invention, the treated plant material has the color and texture of fresh plant material and is substantially free from curling or distortion. The method may comprise five steps including a first step of substantially removing the protective wax coating from flowers and other plant material without adversely affecting the strength of the plant material; a second step comprising a mild oxidative bleach to remove excess color from the plant material; a third step comprising a mild reductive bleach to neutralize any residual oxidative bleach and to stabilize the color; a fourth step comprising the simultaneous preservation and dyeing of the plant material, and a fifth and last step comprising the rinsing and drying of the preserved and dyed material. This may be followed by a $2^{nd}$ preservation and dyeing step and a rinsing and drying. The product can then be rewaxed and stored.

8 Claims, No Drawings

PRESERVATION OF PLANT MATERIAL

CROSS REFERENCE TO RELATED APPLICATIONS

This application is a U.S. National Phase of International Patent Application No. PCT/IB2009/050470 (filed on Feb. 5, 2009), which claims priority to and the benefit of South African Patent Application No. 2008/01238 (filed on Feb. 5, 2008), the entire contents of these applications are incorporated herein by reference.

FIELD OF THE INVENTION

The present invention relates to a method for the preservation and/or dyeing of plant material including cut flowers. In particular, the invention relates to a method including the step of substantially removing the protective wax coating from the plant material before subjecting the material to a bleaching step to remove colour, preferably followed by preservation and dyeing of the material and optionally replacement of the wax.

BACKGROUND OF THE INVENTION

The preservation of cut flowers by means of chemical treatment, which may or may not include a dyeing step, is well known and has been practiced for a long time, as for example, described in PCT International Publication No. WO91/03160 (U.S. Pat. No. 5,252,537), U.S. Pat. No. 6,365,548 and others. However, all of the taught methodologies offer several challenges when attempting to operate on a commercial scale where large quantities of material are required to be treated and where a consistent quality end product is desired. Examples of such challenges include shriveling of flowers and leaves, inconsistent colouring during the dyeing process, inconsistent uptake of preservative (too wet or too dry material), etc.

In the treatment methods disclosed in the prior art, some of the water in the cellular structures of the plant material is removed and replaced with a chemical substance that acts as a humectant, examples of the chemical substance being glycerol and polyethylene glycol, amongst others. The humectant is usually absorbed into the plant material being treated by immersing the stems of freshly cut plant material into a diluted humectant solution in water and allowing the plant material to absorb the humectant by normal plant processes over several hours or days. For certain types of plant material such as firm flower heads, the preservation time may be reduced by submersing the entire plant material in the solution. Alternatively, some or all of the water in the solution may be replaced with a low boiling point solvent, for example ethanol, to increase the rate of evaporation from the leaves and thereby shorten the treatment time required. The excessive use of such solvents is, however, detrimental to cellulose. Such procedures are also difficult to control and often lead to poor quality, shrivelled products.

In addition to the humectant, the solution may contain a dye as required. When a dye is included in the treatment solution, the quality of the final products is often variable (inconsistent colouring and not "life-like") and the colour often fades over time. To overcome some of these shortcomings, plant material may be subjected to one or more bleaching protocols prior to preservation and/or dyeing. Bleaching protocols may, for example, include one or more bleaching steps using oxidative bleaches such as hypochlorite, perborate, chlorine dioxide, hydrogen peroxide, etc. and/or a reductive bleach using, for example, sulfur dioxide, metabisulfite, etc. Problems encountered when including a bleaching step prior to preservation and dyeing includes weakened plant material due to attack of the bleach on the plant cellulose, shriveling of leaves and flower petals, etc.

A need exists to improve the known techniques of plant material preservation and/or dyeing.

SUMMARY OF THE INVENTION

According to a first aspect to the present invention there is provided a method for preserving and/or dyeing plant material, the method comprising the steps of:
 removing the bulk of the natural wax material from the plant material; and
 subjecting the plant material to a bleaching and/or a preservation agent.

In an attempt to improve the process for the preservation of plant material, for example, cut flowers, as described in the prior art, the inventors teach that by substantially removing the protective wax coating on plant material to be preserved and/or dyed by using a suitable solvent, the shortcomings of the dehydration, preservation and dyeing process taught in the prior art can be eliminated.

The term 'the bulk of' is defined to mean at least 50% by weight, preferably at least 60% by weight, more preferably at least 70% by weight, more preferably at least 80% by weight, more preferably at least 90% by weight, most preferably at least 95% by weight.

The method preferably further comprises the step of rinsing the plant material following subjecting the plant material to a bleaching and/or a preservation agent and/or the step of drying and/or storing the plant material.

Preferably the plant material is subjected to an oxidative bleach, which may be a mild oxidative bleach (between 0.5% and 7% by mass).

(The term "% by mass" indicates a mass percentage in mixture.)

The plant material may be subjected to a reductive bleach, which may be a mild reductive bleach (between 0.5% and 5% by mass).

The plant material is preferably exposed to both an oxidative and a reductive bleach and more preferably the plant material is additionally exposed to a preservation agent.

The plant material may be selected from flowers, stems, buds, leaves and foliage.

The method according to this aspect of the invention may further comprise the step of immersing the plant material into a hydrating solution prior to subjecting the plant material to a bleaching and/or a preservation agent. The hydrating solution preferably comprises a solution of nutrients in water and a wetting agent.

The nutrients may consist of sugars selected from glucose, sucrose and dextrose. The amount of nutrient in the hydrating solution is preferably at least about 0.5% by mass. The amount of nutrient in the hydrating solution is preferably no more than about 10% by mass.

The wetting agent is preferably a non-ionic wetting agent and the amount of non-ionic wetting agent in the hydrating solution is preferably at least about 0.001% by mass. The amount of non-ionic wetting agent in the hydrating solution is preferably no more than about 0.1% by mass.

Preferably removing the natural wax material from the plant material is effected with a de-waxing solvent which may be selected from iso-paraffinic solvents and solvent mixtures, petroleum ether and esters of $C_2$-$C_{16}$ carboxylic acids.

The temperature of the de-waxing solvent is preferably at least about 10° C. (degrees Celcius) The temperature of the de-waxing solvent is preferably no more than about 80° C.

The oxidative bleach may be selected from sodium hypochlorite, chlorine dioxide, sodium perborate, hydrogen peroxide and derivatives thereof.

The concentration of the oxidative bleach in mixture is preferably at least about 0.5% by mass. The concentration of the oxidative bleach is preferably not more than about 7.0% by mass.

The pH of the oxidative bleach (when in mixture) is preferably at least about 1. The pH of the oxidative bleach (when in mixture) is preferably no more than about 10.

The pH of the reductive bleach (when in mixture) is preferably at least about 4.0. The pH of the reductive bleach (when in mixture) is preferably no more than about 7.0.

The reductive bleach may be selected from hydrosulfites and hydrides. The hydrosulfites may be selected from sodium hydrosulfite and zinc hydrosulfite.

The hydride is preferably sodium borohydride.

The concentration of the sodium hydrosulfite is preferably at least about 0.5% by mass. The concentration of the sodium hydrosulfite is preferably no more than about 5.0% by mass.

The pH of the sodium hydrosulfite (when in mixture) is preferably at least about 4.0. The pH of the sodium hydrosulfite (when in mixture) is preferably no more than about 7.0.

The temperature of the reductive bleaching agent is preferably no less than about 15° C. The temperature of the reductive bleaching agent is preferably no more than about 65° C.

Preferably the preservation agent comprises a humectant component and a solvent component. The humectant component may be selected from sugars, polyols, polyol-esters, amines and quaternary ammonium compounds and salts of strong and/or weak inorganic and/or organic acids.

The sugars may be selected from sorbitol, dextrose and sucrose. The polyols may be selected from glycerol (glycerine) and mono- or poly-glycols. The polyol-esters may be selected from triacetin and glyceryl triacetate. The amines and quaternary ammonium compounds may be selected from urea and sodium laureth sulfate. The salts of strong and/or weak inorganic and/or organic acids may be selected from calcium chloride and sodium acetate.

The humectant component preferably comprises two or more of a polyol, sugar and a salt of an organic acid. In a preferred embodiment of this aspect to the present invention the humectant component is selected from and including PEG 300 up to PEG 1500, for example, PEG 400, sorbitol, polydextrose and sodium acetate.

The concentration of the preservation agent is preferably at least about 10% by mass. The concentration of the preservation agent is preferably no more than about 90% by mass (in a suitable solvent solution, for example aqueous).

The solvent component may be selected from water, alcohols including ethanol, n-propanol, iso-propyl alcohol, n-butanol, tert-butanol, petroleum ethers and iso-parrafins.

Preferably the solvent component is a mixture comprising water, ethanol and iso-propyl alcohol. In a preferred embodiment the proportions of the solvent component are in the ranges of: water (about 5-15%); ethanol (about 5-25%) and iso-propyl alcohol (about 5-80%) by mass.

The preservation agent may also comprise a dye, a fungicide and/or a fragrance material.

The temperature of the preservation agent is preferably at least about 20° C. The temperature of the preservation agent is preferably no more than about 100° C.

The preservation agent (solution) is preferably pressurized with an inert gas to increase the rate of uptake. The inert gas may be selected from either nitrogen and/or carbon dioxide and the pressure of the inert gas is preferably at least about 50.66 and no more than about 202.65 kPa.

Preferably the drying process is performed under conditions of laminar air flow, for example, by blowing hot air through the drying chamber. The temperature of the drying process is preferably in the range of about 30° C.-100° C. The rate of air flow is preferably in the range of about 0.2-1.5 m/s.

According to a second aspect to the present invention there is provided preserved plant material wherein the natural wax material of the plant material is substantially removed.

According to a third aspect to the present invention there is provided preserved plant material prepared by a method as hereinbefore described.

This invention therefore relates to a method for the preservation and/or dyeing of plant material including cut flowers. According to the invention, the treated flowers and/or plant material have the colour and texture of fresh plant material and are substantially free of cell damage and curling or distortion. The method according to the present invention preferably comprises five steps which comprise:

a first step of substantially removing the protective wax coating from flowers and other plant material without adversely affecting the strength of the plant material;

a second step comprising treating the plant material with a mild oxidative bleach to remove excess colour from the plant material;

a third step comprising treating the plant material with a mild reductive bleach to neutralize any residual oxidative bleach and to stabilize the colour;

a fourth step comprising preservation of the plant material wherein dyeing of the plant material could be included or excluded; and a fifth comprising the rinsing and drying of the preserved and dyed material.

An optional second preservation step, which would normally include dyeing may be the sixth step followed by the seventh step, namely a rinse, then a further drying step. The final step may be the rewaxing of the plant material.

The invention also teaches preserved plant material wherein the natural wax material has been substantially removed from the plant material. The plant material is preferably preserved by a method according to the present invention.

Whilst the prior art teaches a dehydration step using various solvents, the present invention teaches that these dehydration steps result in the excessive use of solvents that causes structural damage of plant material (tissue and cells) and so affects the quality of the final product. The prior art uses the principle of dehydration and replacing the fluids in the plant tissue with a solvent followed by a preservation step wherein the solvent in the plant tissue is replaced with a preservative.

The present invention on the other hand takes a "soft" approach and limits the use and application of solvents and other harsh chemicals to plant tissue as far as possible in order to mitigate the damage caused to plant tissue and cells. The dewaxing step allows for more effective bleaching of the plant material with lower concentrations of oxidising solution and for shorter durations and eliminates the need for dehydration all together.

The use of a separate bleaching step also avoids the adding of bleach chemicals to the preservation chemicals. This addition is difficult to control and manage in production. It is also a fire and explosion risk.

DETAILED DESCRIPTION OF THE INVENTION

The present invention relates to a significantly improved process for the chemical preservation and dyeing of plant material, for example, flowers to give a final product having an appearance and texture comparable to that of a fresh live material (flowers). The process of this invention preferably comprises the following steps:

a) Selecting, and cutting of flowers and/or plant material for the preservation process, and assembling such plant material onto suitable supporting devices such as support grids or trays for supporting the shape of the flowers and to keep the calyx in upright position;

b) Removing the protective wax coating from the plant material to be preserved and/or dyed by immersion into, or spraying with a suitable de-waxing solvent to remove natural waxes from the stems, leaves and/or flower heads and petals;

c) Subjecting the de-waxed plant material to a short and mild oxidative bleach by immersion into, or spraying with a dilute aqueous oxidizing bleaching agent;

d) Subjecting the bleached plant material to a reductive bleaching agent to destroy residual oxidative bleach and to stabilize the colour of the final dyed material by immersion into, or spraying with a dilute aqueous reducing bleaching agent;

e) Preserving the bleached and stabilized plant material by immersion into, or spraying with a suitable preservation solution that may also contain a dye of choice;

f) Rinsing the preserved plant material to remove excess dye and preserving solution from the plant material's surfaces;

g) Drying and storing of the preserved plant material; and optionally h) A second preservation step that may contain a dyeing step;

i) Rinsing the plant material;

j) Drying the plant material; and k) Rewaxing the plant material.

The above-mentioned steps are each described in detail below:

(a) Selecting and cutting of flowers and/or plant material for the preservation process and assembling such plant material onto suitable supporting devices such as grids;

This step consists of selecting and cutting healthy looking plant material at the desired developmental stage of the plant (e.g. a proper opening stage of the flower). The stems of freshly cut plant material should be immersed into a suitable hydrating solution until such time that the plant material is being processed for the preservation process. Suitable hydrating solutions comprise a solution of suitable nutrients in water to which a small amount of wetting agent has been added.

While any of the great number of additional nutrients known to the art may be used in the present treatment composition, the preferred nutrients of this invention consist mainly of sugar, such as glucose, sucrose or dextrose. The sugar provides a source of nutrition capable of being utilized by the flower or other plant material so that it will retain freshness and normal plant activity until the preservation process is started. The preferred nutrients are glucose and sucrose, either alone or in combination.

The amount of nutrient in the hydrating solution is not critical, but should preferably be in the range 0.5-10% by mass and more specifically in the range 0.5-5% by mass.

It is also preferred for the hydrating solution to contain a small amount of wetting agent, preferably a non-ionic wetting agent, in order to assist keeping fluid carrying vessels and tissues soft and firm, especially during the processing period when the plant material is taken out of the hydrating solution. Any commercial, non-ionic wetting agent known in the art can be used. The amount of wetting agent should be such that it is effective in maintaining the functions of the fluid carrying vessels and tissue, yet not too much to interfere with the absorption and retention of the preservation solution.

The amount of wetting agent should preferably be in the range of 0.001-0.1% by mass and more specifically in the range 0.001-0.03% by mass.

The plant material may be treated either as whole units such as flowers attached to stems, or separated into smaller parts. In either case, the plant material should be supported onto a suitable supporting frame so as to prevent or minimize deformation of the plant material during the entire preservation process. Persons skilled in the art will realize that many different forms of support, made of a wide variety of material, can be used as supporting framework. It is, however, desirable that supporting frameworks not contain metallic parts that would come in direct contact with the plant material during the preservation process.

(b) Removing the protective wax coating from the plant material to be preserved and/or dyed by immersion into, or spraying with a suitable de-waxing solvent to remove natural waxes from the stems, leaves and/or flower petals;

This step consists of removing the natural protective wax coating on the plant material to be preserved by either immersing the supported plant material into a bath containing a suitable de-waxing solution, or alternatively spraying the supported plant material with a suitable de-waxing solution. The removal of the protective wax coating from such plant material before the actual preservation process offer many advantages over other processes known in the art that do not contain such a de-waxing step, including: removal of the bulk of coloured material from leaves and flower petals without bleaching; reducing the severity of the subsequent bleaching step which could weaken the plant material's internal cellulose structure; providing a suitably prepared surface for the attachment of dyes thereby resulting in consistent and even colours; providing a larger available area through which preserving solution may be absorbed into the plant material.

While many solvents and solvent mixtures known in the art may be used to remove the protective wax coating from the surfaces of plant material, solvents for the purpose of this invention should have several desirable properties, including:

be effective in removing the natural wax coating on plant material surfaces;

be effective in removing surface coloured bodies from plant material surfaces;

be non-polar;

be non-toxic;

have a high flash point;

have a low viscosity;

be easily recoverable; and be environmentally benign.

Furthermore, the use of the solvent should not weaken the plant material to a significant degree, nor interfere with the subsequent steps of the preservation process. Solvents and solvent mixtures that meet these criteria and which are preferred for the purpose of this invention include iso-parafinic solvents and solvent mixtures, petroleum ether, esters of C2-C16 carboxylic acids, either alone or in mixtures with other solvents.

The method of applying the solvent to the plant material for the purpose of dewaxing is not critical and may, for example, be by means of immersing the supported plant material into a bath of solvent, or by spraying the solvent onto the supported plant material.

Persons skilled in the art will realise that the length of time used for de-waxing will depend on several factors, including the type of plant material being treated (since some plants have a thicker wax layer than others), the part of the plant being treated (e.g. stem or flower head) and the solvent temperature. When higher solvent temperatures are used, treatment times may be reduced. Temperatures ranging from 10° C. to 80° C. is preferable, and more specifically temperatures between 10° C. and 60° C. The shorter the duration, the less the risk of causing cellulose damage.

Dewaxing improves impregnation efficiency and reduces the need for dehydration. Dewaxing also reduces the application and exposure of harsh solvents that cause tissue damage.

(c) Subjecting the de-waxed plant material to a short and mild oxidative bleach by immersion into, or spraying with a dilute aqueous oxidizing bleaching agent;

This step involves the bleaching of the de-waxed plant material by application of an oxidative bleach. Oxidative bleaches act by breaking down the coloured compounds into smaller, colourless compounds. Although these bleaches are very effective, they may cause structural damage to the plant material by breaking down lignin, thereby resulting in a weak and soft end product. Thus, these bleaches require careful use to avoid a brittle and weak final product.

It is an advantage of the present invention that the conditions under which bleaching of plant material are carried out can be reduced significantly due to the introduction of a prior de-waxing step, thereby reducing cost, improve safety of operations, reduce treatment times, and improve product appearance.

Persons skilled in the art will realize that any one of the several commercially available oxidative bleaches can be used to achieve the purpose of this invention, including sodium hypochlorite, chlorine dioxide, sodium perborate, and hydrogen peroxide (or derivatives such as sodium peroxide). However, preferred bleaches are those that are easy to handle and store, do not pose significant health and safety risks when used under appropriate conditions and are not detrimental to the environment. Bleaches that are especially suited for this purpose include hydrogen peroxide and chlorine dioxide solutions.

The preferred concentration of bleach and the length of bleaching time depend on (a) the type of plant material to be bleached and (b) the degree of bleaching required. Thus, plant material that will be subsequently dyed in a light colour, or plant material that needs to be white, will require a longer bleaching period and/or a stronger bleaching solution than plant material to be subsequently bleached in a darker colour. Preferred concentrations of the bleach vary between 0.5 and 7.0% by mass, but more preferably between 1.0 and 4.0%. The bleaching time generally may vary from 1 minute to 30 minutes.

Persons skilled in the art will know that control of the pH of the bleaching solution is vital for effective and cost-efficient bleaching. Bleach chemicals release their bleaching power as they decompose. A slow rate of decomposition is desirable because it allows the active chemicals time to diffuse through the plant material to the pigments which are to be destroyed. For bleaching with chlorine dioxide solutions, the preferred pH range is between a pH of 1 and 10, but preferably in the pH range 5.0-9.0. For bleaching with hydrogen peroxide, the preferred pH range is between 7.5 and 12.5, preferably in the range 8.0-11.0.

Persons skilled in the art will also know that the temperature at which bleaching is performed can influence both the rate and the efficiency of the bleaching process. Thus, irrespective of the type of bleach used, the higher the bleaching temperature, the faster the rate of bleaching. Thus, the temperature selected for the beaching of different types of plant material need to consider both the type of material to be bleached, as well as the degree of bleaching required. Too high a bleaching temperature for soft plant material will make controlling the bleaching time difficult and lead to over-bleaching and softening of the plant material. Too low a bleaching temperature, however, may require excessive bleaching times to achieve the desired degree of bleaching. The preferred temperature range will therefore vary, depending upon the type of plant material to be bleached, the degree of bleaching required, and the optimum bleaching time to process the plant material. Typically bleaching temperatures will fall in the temperature range from about 15° C. to about 65° C.

The method of applying the bleaching solution to the plant material is not critical and may, for example, be by means of immersing the supported plant material into a bath of bleaching solution, or by spraying the bleaching solution onto the supported plant material.

(d) Subjecting the bleached plant material to a reductive bleaching agent to destroy residual oxidative bleach and to stabilize the colour of the final dyed material by immersion into, or spraying with a dilute aqueous reducing bleaching agent.

The purpose of this step is to (a) increase the degree of bleaching of the plant material without causing damage to the plant material; (b) destroying residual oxidative bleach carried over from the oxidative bleach step; and (c) increase the colour stability of the final preserved plant material.

Reductive bleaches do not degrade the coloured compounds, but instead chemically modify them into colourless compounds. These bleaches do less damage to the plant structure, but can cause yellowing of the plant material when used in isolation, and which can lead to a poor quality preserved product.

Examples of reducing bleaches that can be used in the process of this invention includes the so-called hydrosulfites (e.g. sodium hydrosulfite and zinc hydrosulfite), and hydrides (e.g. sodium borohydride). The use of sodium hydrosulfite is preferred for the process of this invention.

The preferred concentration of bleach and the length of bleaching time again depends on the type of plant material to be bleached and the degree of bleaching required. Thus, plant material that will be subsequently dyed in a light colour, or plant material that needs to be white, will require a longer bleaching period and/or a stronger bleaching solution than plant material to be subsequently bleached in a darker colour. Preferred concentrations of the sodium hydrosulfite bleach vary between 0.5 and 5.0%, but more preferably between 1.0 and 4.0%. The bleaching time generally may vary from 1 minute to 30 minutes.

As in the case of the oxidative bleach step, control of the pH of the bleaching solution is vital for effective and cost-efficient bleaching. The preferred pH range for the sodium hydrosulfite bleach step is between a pH of 4.0 and 7.0, but preferably in the pH range 5.0-6.5.

The preferred temperature range for the sodium hydrosulfite bleach step may, as in the case of the oxidative bleaching step, vary depending upon the type of plant material to be bleached, the degree of bleaching required, and the optimum bleaching time to process the plant material. Typically bleaching temperatures will fall in the temperature range from about 15° C. to about 65° C.

The method of applying the bleaching solution to the plant material is not critical and may, for example, be by means of immersing the supported plant material into a bath of bleaching solution, or by spraying the bleaching solution onto the supported plant material.

(e) Preserving the bleached and stabilized plant material by immersion into, or spraying with a suitable preservation solution that may also contain a dye of choice.

The purpose of this step of the process of the invention is to replace some part of the water contained within the plant material with a suitable humectant that would keep the plant material supple for extended periods of time. Optionally, this step may also include the addition of a dye solution to the preserving solution to provide for a colourful end product that has a consistent colouring.

Persons skilled in the art will know that the selection of a suitable humectant is critical in the process of preserving plant material as the selection of the type of humectant largely determines the quality of the final product in terms of look, feel and durability. The following are some of the desired characteristics of a suitable humectant:

It must be non-toxic;
It must have a sufficient water holding capacity over a wide range of relative humidity conditions;
It must not lead to "bleeding" under high humidity conditions;
It must not cause excessive discolouration of final preserved plant material products, or cause dyed plant material to fade;
It must be retained within the structure of plant material for sufficiently long periods of time;
It must be readily absorbed by the plant material; and
It must be cost effective.

None of the known humectants used for the preservation of plant material individually meet all the desired characteristics listed above. One way to overcome this is to use a combination of two or more different humectants that will meet most of these requirements. When used in combination, it is important that the relative proportions of humectants be carefully chosen to meet those characteristics specifically desired.

Humectants which are suitable for use in the process of this invention, either alone or in combination include compounds from the following classes: sugars (such as sorbitol, dextrose, sucrose, etc.); polyols (e.g. glycerol (glycerine), mono- or poly-glycols, etc.), polyol-esters (e.g. triacetin, glyceryl triacetate, etc.); amines and quaternary ammonium compounds (e.g. urea, sodium laureth sulfate, etc.); and salts of strong and weak inorganic and organic acids (e.g. calcium chloride, sodium acetate, etc.). For the purpose of the present invention, it is preferred that a mixture of humectants be used, comprising two or more of a polyol, sugar, and salt of an organic acid. Examples of preferred humectants include PEG 300, PEG 400 and up to PEG 1500, sorbitol, polydextrose, sodium acetate, etc.

The long-term flexibility of preserved plant material depends to a large degree on the type and the amount of humectant absorbed into the plant material. In general, the purpose is to maintain the water content of plant material above about 15% to ensure flexibility. The amount of humectant absorbed should therefore be capable of retaining at least this minimum amount of water inside the plant. This objective may be achieved to allow the plant material to absorb a humectant solution and then allowing the excess solvent to evaporate from the plant material. The concentration of the humectant solution should be in the range 10-90% by mass, and preferably in the range 10-80% by mass. The less solvent used, the less the risk of cell damage.

The duration of this step is typically 4 to 48 hrs.

Solvents suitable for carrying the humectant mixture into the plant material include water, alcohols such as ethanol, n-propanol, iso-propyl alcohol, n-butanol, tert-butanol, petroleum ethers, and iso-parrafins. It is a preferred embodiment of this invention that a mixture containing water, ethanol, and iso-propyl alcohol be used as solvent for the humectant solution. The preferred proportions of the solvent components should be in the ranges: water 5-15%; ethanol 5-25%; and iso-propyl alcohol 5-80% by mass.

Apart from the humectant components and the solvent components, the preservative solution may optionally contain other additives to impart desirable properties to the preserved plant material. Such additives may for example include a dye to impart a desirable colour, a fungicide to prevent mildew growth, and a fragrance material to impart a desirable odour. The types of additive are not restricted, for example dyes may either be a food type dye, a flower dye, a textile dye, etc.

The method used for allowing the plant material to absorb the preservative solution is also not restricted, and may for example include submersion of the entire plant material to be preserved underneath the preservative solution, or allowing the stems of the plant material to be preserved to stand in a solution of the preservative solution.

The length of time required for plant material to absorb sufficient preservative solution to remain supple for extended periods of time will vary with the type of plant material to be preserved, the method used for uptake of preservative solution, as well as the conditions under which the preservation process is carried out. Thus, softer plant material and plant material with large foliage surface areas such as flowers and leaves will require a shorter treatment period than plant material that hard or woody and which have smaller foliage surface areas. In addition, uptake by submersion of plant material beneath the surface of a preservative solution will require shorter treatment times compared to the stem uptake method where the stems of the plant material is allowed to stand in a solution of the preservative solution.

Additionally, the conditions under which the preservation process is carried out will also influence the times required for sufficient uptake of preservative solution. Thus, preservative solutions above ambient temperature will reduce the uptake time as compared to preservative solutions at ambient temperature. For the purpose of this invention, it is preferred that the temperature of the preservative solution be raised above room temperature. Preferred preservative solution temperatures are between 25-100° C., and preferably between 25 and 85° C.

Similarly, preservative solutions containing the plant material may also be pressurized with a suitable inert gas to increase the rate of uptake of preservative solution. Suitable inert gasses that can be used for compression according to the present invention include nitrogen and carbon dioxide. Preferred pressures vary between 0.5-2.0 atm of pressure.

(f) Rinsing the preserved plant material to remove excess dye and preserving solution from the plant material's surfaces;

The purpose of this step of the preservation process is to remove excess preservative solution and other additives contained in the preservative solution from the external surfaces of the preserved plant material. This purpose is achieved by rinsing the preserved plant material with a solvent not containing any humectant or other additives. The same solvents previously elaborated on for the make-up of the preservative solution are preferred for this part of the process.

The rinsing method is not restricted and may for example be by dipping into a bath of the rinsing solvent, or by spraying the preserved plant material with the rinsing solvent.

(g) Drying and storing of the preserved plant material.

The purpose of this part of the process is to remove excess solvent from the external plant surface as well as from the internal plant structures. Additionally the drying stage also serves to fix the dye, if such has been used during the preservation step, onto the preserved plant material.

The temperature of the drying process should be sufficient to remove the solvent but not the humectant from these surfaces. Preferred temperatures are between 30° C. to about 100° C., more specifically between 40° C. and 90° C.

To assist the removal of solvent from plant surfaces, it is preferable that drying is performed under conditions of laminar air flow, for example by blowing hot air through the drying chamber. The rate of air flow is not critical, but should preferably be in the range 0.2-1.5 meters per second.

The drying time should be sufficient to remove the bulk of the solvent from plant surfaces, typically between 30 minutes and twelve hours, depending on the type of plant material to be dried and the drying temperature being used.

The remaining optional steps are discussed hereunder.

h) The plant material can then be subjected to a $2^{nd}$ preservation step as described above in which a dye can be added. This preservation step would typically have a higher concentration of humectant than that applied in the $1^{st}$ preservation step.

i) The plant material may then be subjected to a $2^{nd}$ rinse as described above.

j) The plant material may then be dried.

k) The plant material may then be subjected to a rewaxing step.

l) The treated plant material may then be stored as described above. The temperature and humidity preferably needs to be controlled and managed in the storage to avoid damage to plant material.

The following examples serve to illustrate the preferred embodiments of the present invention and should not be construed to limit the scope and application thereof in any manner whatsoever.

ILLUSTRATIVE EXAMPLES

Example 1

Investigating the Medium to Remove the Natural Wax

In order to determine the best solvent to use for de-waxing plant material, fresh cut flower heads were placed on top of spikes and immersed into a bath containing various solvents such as hexane, toluene, petroleum ether, iso-parrafins, etc. for a period of 3 minutes at room temperature. The flower heads were then allowed to drip dry before they were subjected to a short bleach in a sodium hypochlorite bleach bath (room temperature, 3 minutes). The bleached flowers so obtained were compared to flowers subjected to exactly the same bleaching step, but omitting the de-waxing step. In all cases, the degree of bleaching achieved after de-waxing was significantly higher than without dewaxing. Some solvents such as hexane and toluene, however, result in brittle petals and/or shrivelled petals, but petroleum ether and iso-parrafin solvents gave results in supple petals free of any shrivelling.

Example 2

Investigation of Bleaching Agents

Fresh cut flowers were placed on top of spikes and immersed into a bath containing iso-paraffin for 3 minutes, after which they were allowed to drip dry. The de-waxed cut flowers were then submersed into a bath containing different oxidative bleaching agents, including sodium hypochlorite, chlorine dioxide, sodium perborate and hydrogen peroxide. The pH was regulated separately for each different bleaching agent. The flower heads were then allowed to drip dry before placing into a bath containing a reducing bleach of sodium metabisulfite medium. The bleaching time generally may vary between 1-3 minutes. The results obtained showed that all of the oxidative bleaching agents gave essentially the same degree of bleaching; however, chlorine dioxide and hydrogen peroxide resulted in flowers with a "stronger", more silky feel product.

Example 3

Investigation of the Preservation Solution

Fresh cut flowers were placed on top of spikes and treated as described in example 2 above. The bleached flower heads so obtained were placed into various preservative mixtures containing an alcohol (ethanol, n-propanol or iso-propanol) to which was added water (0-20%) and humectant (polyethylene glycol 200, 300, 400, 600, 1,4-butane diol, or 1,3-butane diol), surfactant (Teepol), and one or more salts (NaCl, $CaCl_2$, NaOAc, etc). In addition, when preferred, various mixtures of dyes were also added to the preservative bath solution, for example:

| | |
|---|---|
| Mixture A: | Colouring matter: Clarke's Red (5-10%) |
| | Colouring matter: Clarke's Plum (1-3%) |
| Mixture B: | Master Mix Textile dyes |
| | Colouring matter: Textile dye Pink-Red (325-425 mL) |
| | Colouring matter: Textile dye Orange-Red (325-425 mL) |
| | Colouring matter: Textile dye Blue-Red (7.5-12.5 mL) |

Following preserving for a period of 2-8 hours, flowers were rinsed with iso-propanol and dried. The preserved flowers so obtained were compared with each other in terms of look, and feel to determine the best combination of preservative solution.

The invention claimed is:

1. A method for preserving and/or dyeing plant material, the method consisting of:
    a first step of removing at least 50% by weight of the natural wax material from the plant material, wherein removing natural wax material from the plant material is achieved by treating the plant material with a non-polar de-waxing solvent consisting of iso-paraffin, petroleum ether, esters of C2-C16 carboxylic acids, or mixtures thereof;
    a further step of immersing the plant material into a hydrating solution;
    a further step of subjecting the plant material to a bleaching agent and a pressurized preservation agent, wherein the preservation agent consists essentially of a humectant component, a solvent component and optionally a dye, fungicide or a fragrance material;
    a further step of rinsing the plant material; and
    a further step of step of drying and/or storing the plant material.

2. The method as claimed in claim 1 wherein the bleaching agent is an oxidative bleach and/or a reductive bleach.

3. The method as claimed in claim 1 wherein the plant material is selected from flowers, stems, buds, leaves, foliage.

4. The method as claimed in claim 1 wherein the humectant component is selected from sugars, polyols, polyol-esters, amines and quaternary ammonium compounds and salts of strong and/or weak inorganic and/or organic acids.

5. The method as claimed in claim 1 wherein the humectant component comprises two or more of a polyol, sugar and a salt of an organic acid.

6. The method as claimed in claim 1 wherein the solvent component is selected from water, alcohols including ethanol, n-propanol, iso-propyl alcohol, n-butanol, tert-butanol, petroleum ethers and iso-paraffins.

7. The method as claimed in claim 1 wherein the preservation agent includes a dye, a fungicide or a fragrance material.

8. The method as claimed in claim 1 wherein the preservation solution is pressurized with an inert gas to increase the rate of uptake.

\* \* \* \* \*